United States Patent [19]

Schwalge et al.

[11] Patent Number: 5,013,354
[45] Date of Patent: May 7, 1991

[54] 3-PHENYLPROPIONIC ACID DERIVATIVES

[75] Inventors: Barbara Schwalge, Ludwigshafen; Peter Plath, Frankenthal; Karl Eicken, Wachenheim; Norbert Meyer, Ladenburg; Bruno Wuerzer, Otterstadt, all of Fed. Rep. of Germany

[73] Assignee: BASF Aktiengesellschaft, Ludwigshafen, Fed. Rep. of Germany

[21] Appl. No.: 217,167

[22] Filed: Jul. 11, 1988

[30] Foreign Application Priority Data

Jul. 23, 1987 [DE] Fed. Rep. of Germany ....... 3724395

[51] Int. Cl.$^5$ ............... C07D 209/48; A01N 43/38
[52] U.S. Cl. ........................................ 71/95; 548/513
[58] Field of Search ........................... 548/513; 71/95

[56] References Cited

U.S. PATENT DOCUMENTS 3,984,435 10/1976 Matsui ................................ 548/513
4,439,229 3/1984 Swithenbank .

FOREIGN PATENT DOCUMENTS 3603789 8/1987 Fed. Rep. of Germany .
0007602 12/1987 PCT Int'l Appl. .
1077194 7/1967 United Kingdom .

Primary Examiner—Robert A. Wax
Assistant Examiner—Fred Tsung
Attorney, Agent, or Firm—Oblon, Spivak, McClelland, Maier & Neustadt

[57] ABSTRACT 3-phenylpropionic acid derivatives of the general formula I

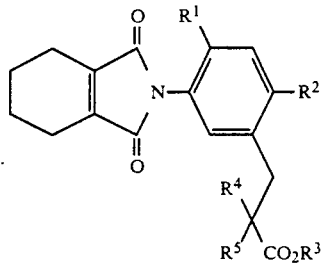

where $R^1$ is hydrogen or halogen, $R^2$ is halogen, $R^3$ is unsubstituted or halogen-, $C_1$-$C_4$-alkoxy- or $C_1$-$C_4$-alkylthio-substituted $C_2$-$C_6$-alkyl, $C_5$-$C_7$-cycloalkyl-substituted $C_1$-$C_6$-alkyl, further $C_5$-$C_7$-cycloalkyl, $C_3$-$C_6$-alkenyl or $C_3$-$C_6$-alkynyl or, together with $R^4$, a $C_2$-$C_4$-alkylene chain, $R^4$ is hydrogen or unsubstituted or halogen-, $C_1$-$C_4$-alkoxy-, $C_1$-$C_4$-alkylthio- or $C_5$-$C_7$-cycloalkyl-substituted $C_1$-$C_6$-alkyl; $C_3$-$C_7$-cycloalkyl; unsubstituted or halogen-substituted $C_3$-$C_6$-alkenyl or $C_3$-$C_6$-alkynyl or halogen or $R^4$, together with $R^5$ and the carbon atom of this substituent, is $C_3$-$C_6$-cycloalkyl which may be interrupted by an oxygen or a sulfur atom, $R^5$ is unsubstituted $C_1$-$C_6$-alkyl or halogen-, $C_1$-$C_4$-alkoxy- or $C_1$-$C_4$-alkylthio-substituted $C_2$-$C_6$-alkyl; cyano or acyl ($COR^6$) or alkoxycarbonyl ($CO_2R^7$), $R^6$ denoting $C_1$-$C_6$-alkyl or, together with $R^4$, a $C_3$-$C_5$-alkylene chain and $R^7$ denoting unsubstituted or halogen-, $C_1$-$C_4$-alkoxy- or $C_1$-$C_4$-alkylthio-substituted $C_2$-$C_6$-alkyl or unsubstituted or $C_5$-$C_7$-cycloalkyl-substituted $C_1$-$C_6$-alkyl, further $C_5$-$C_7$-cycloalkyl, $C_3$-$C_6$-alkenyl or $C_3$-$C_6$-alkynyl, with the proviso that $R^1$ and $R^4$ do not simultaneously denote hydrogen when $R^5$ is cyano or $CO_2R^7$, processes for their manufacture, and their use as herbicides.

6 Claims, No Drawings

3-PHENYLPROPIONIC ACID DERIVATIVES

DE-A-15 42 777 discloses that substituted phenylpropionic acids possess herbicidal activity. Similar compounds, for example compound A shown below, are described in EP-A-68 822

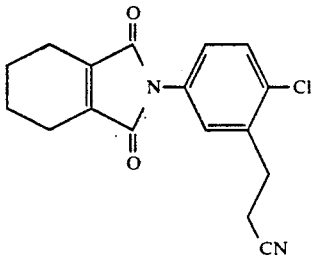

Particularly for use next to crops, for example by the post-emergence method, it is, however, desirable to have compounds which have fairly high selectivity in combination with a low application rate. We have found that substituted phenylpropionic acid compounds of the general formula I

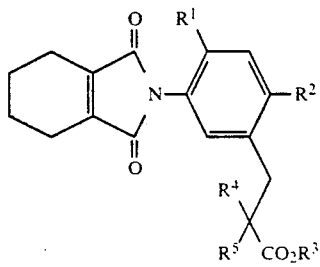

where $R^1$ is hydrogen or halogen, $R^2$ is halogen, $R^3$ is $C_2-C_6$-alkyl which is unsubstituted or substituted by halogen, $C_1-C_4$-alkoxy or $C_1-C_4$-alkylthio or is $C_5-C_7$-cycloalkyl-substituted $C_1-C_6$-alkyl or is $C_5-C_7$-cycloalkyl, $C_3-C_6$-alkenyl or $C_3-C_6$-alkynyl or, together with $R^4$, forms a $C_2-C_4$-alkylene chain, $R^4$ is hydrogen or $C_1-C_6$-alkyl which is unsubstituted or substituted by halogen, $C_1-C_4$-alkoxy, $C_1-C_4$-alkylthio or $C_5-C_7$-cycloalkyl or is $C_3-C_7$-cycloalkyl or is unsubstituted or halogen-substituted $C_3-C_6$-alkenyl or $C_3-C_6$-alkynyl or halogen, or $R^4$ together with $R^5$ and the carbon atom of this substituent forms $C_3-C_6$-cycloalkyl which may be interrupted by an oxygen atom or a sulfur atom, $R^5$ is unsubstituted $C_1-C_6$-alkyl or $C_2-C_6$-alkyl which is substituted by halogen, $C_1-C_4$-alkoxy or $C_1-C_4$-alkylthio or is cyano, acyl ($COR^6$) or alkoxycarbonyl ($CO_2R^7$), where $R^6$ is $C_1-C_6$-alkyl or, together with $R^4$, forms a $C_3-C_5$-alkylene chain and $R^7$ is $C_2-C_6$-alkyl which is unsubstituted or substituted by halogen, $C_1-C_4$-alkoxy or $C_1-C_4$-alkylthio or is unsubstituted or $C_5-C_7$-cycloalkyl-substituted $C_1-C_6$-alkyl or is $C_5-C_7$-cycloalkyl, $C_3-C_6$-alkenyl or $C_3-C_6$-alkynyl, with the proviso that $R^1$ and $R^4$ cannot simultaneously be hydrogen when $R^5$ is cyano or $CO_2R^7$, have an advantageous herbicidal action, particularly in the postemergence method, and are selective with respect to a number of crops.

In formula I, halogen is fluorine, chlorine or bromine, halogen radicals $R^1$ preferably being fluorine and halogen radicals $R^2$ preferably being chlorine or bromine.

Alkyl (alone or as part of a substituent) includes branched and straight-chain radicals. Examples are methyl, ethyl, n-propyl, isopropyl, n-butyl, sec-butyl, isobutyl and the higher homologs, pentyl, hexyl, etc., together with their isomers. Accordingly, alkanoyls and cyanoalkyls contain an additional carbon atom.

The alkenyl and alkynyl radicals may likewise be branched or straight-chain. Examples of alkenyl radicals in formula I are allyl, 2-propenyl, 2-butenyl, 3-butenyl, 2-isobutenyl, 2-pentenyl, 3-pentenyl and 4-pentenyl, in particular allyl or 2-butenyl. Alkynyl radicals are, as a rule, propargyl, 2-butynyl, 3-butynyl and isomeric pentynyl radicals; however, alkynyl is preferably propargyl or 2- or 3-butynyl.

As a substituent of the general formula I, alkoxy is methoxy, ethoxy, n-propoxy, isopropoxy or the four isomeric butoxy radicals, in particular methoxy, ethoxy or isopropoxy. Examples of alkylthio in the formula I are methylthio, ethylthio, n-propylthio, isopropylthio and n-butylthio, in particular methylthio and ethylthio, and cycloalkyl is cyclopropyl, cyclobutyl, cyclopentyl, cyclohexyl or cycloheptyl. Cycloaliphatic radicals correspond to these ring systems.

An alkylene chain is, in particular, the propylene, butylene or pentylene chain. In these chains, each group, apart from the terminal methylene groups, can be replaced by an oxygen or sulfur atom. Methyleneoxamethylene, methyleneoxaethylene, methyleneoxapropylene and ethyleneoxaethylene chains are preferred examples of oxygen-containing groups, and methylenethiamethylene, methylenethiaethylene, methylenethiapropylene and methylenethiaethylene chains are preferred examples of the corresponding sulfur-containing substituents.

The phenylpropionic acid derivatives of the formula I can be described as N-tetrahydrophthalimides; accordingly, they are obtainable from 3,4,5,6-tetrahydrophthalic anhydride and an aniline derivative of the formula VI, for example in a solvent at from 20° to 200° C., preferably from 40° to 150° C. Examples of suitable solvents are lower fatty acids, such as glacial acetic acid or propionic acid, or aprotic solvents. When aprotic solvents are employed, a water separator is advantageously used.

Preferred compounds I are those in which $R^1$ is hydrogen or fluorine and $R^2$ is chlorine or bromine, and $R^1$ and $R^4$ cannot simultaneously be hydrogen when $R^5$ is cyano or a carboxylic acid radical $CO_2R^7$.

The aniline derivatives of the formula VI can be obtained, for example, by nitrating an appropriately substituted carboxylic ester derivative IV and then reducing the resulting nitrobenzene V with tin(II) ions or with iron:

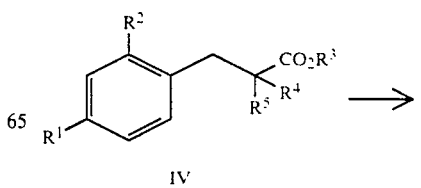

IV

-continued

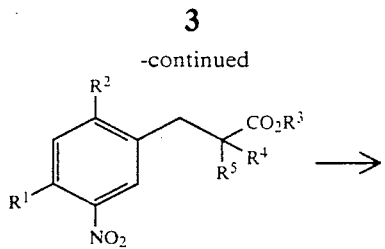
V

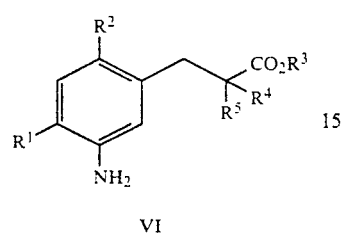
VI

The reduction can also be carried out by catalytic hydrogenation using a noble metal catalyst, such as platinum or palladium, under relatively mild conditions.

The necessary phenylpropionates of the formula IV which are substituted in the nucleus can be prepared in various ways, for example:

(a) if $R^5$ is cyano, $COR^6$ or $CO_2R^7$: by reacting an appropriate benzyl halide II, preferably a chloride or bromide, in a conventional manner in the presence of a base, with or without the addition of a catalyst and in a two-phase system, by the method stated in Chem. Ind. 18 (1978), 731, with a carboxylic acid derivative of the formula III.

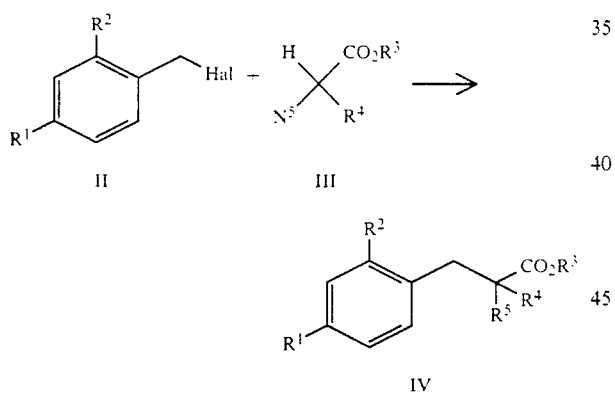
IV

This reaction is carried out in an aprotic solvent, e.g. toluene, acetonitrile or dimethylformamide, under two-phase conditions using an inorganic base, such as sodium hydroxide or potassium hydroxide, in the presence of a phase-transfer catalyst; crown ethers, such as 15-crown-5 or 18-crown-6, or corresponding benzofused derivatives, such as dibenzo-18-crown-6, are preferably used. In some cases, it is also possible to use polyethylene glycol dialkyl ethers of the type

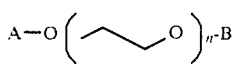

(where n is 5–7 and A and B independently of one another are each $C_1$–$C_4$-alkyl) or quaternary ammonium salts;

(b) if $R^5$ is cyano, $COR^6$ or $CO_2R^7$: by reacting an appropriate 3-phenylpropionic acid derivative of the formula VII, obtainable, for example, from the parent cinnamic acid, in the presence of a base in a solvent, by the methods stated in Organic Reactions 9 (1957), 107, with a halide of the formula VIII, preferably an iodide or bromide.

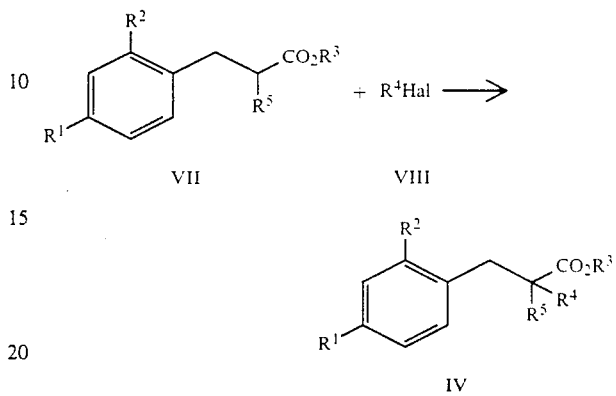
VII   VIII
IV

Compounds of the type IV in which $R^4$ is halogen are preferably prepared in an organic solvent in a conventional manner by reaction with a sulfuryl halide.

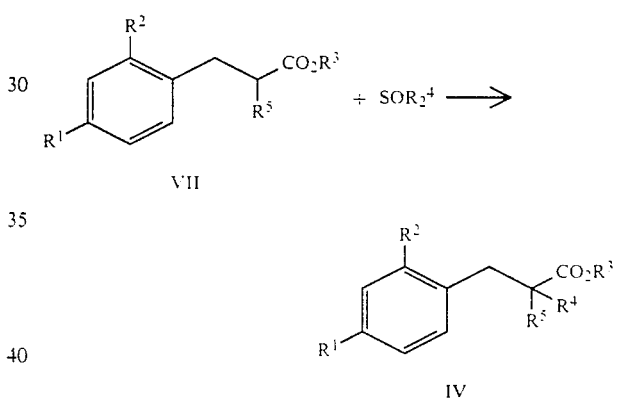
VII
IV

Suitable solvents are carboxylic acids, e.g. glacial acetic acid or propionic acid, and hydrocarbons, e.g. toluene. In this case, $R^4$ is preferably chlorine or bromine.

In this case, it is also possible alternatively to start from a nitrocompound XII

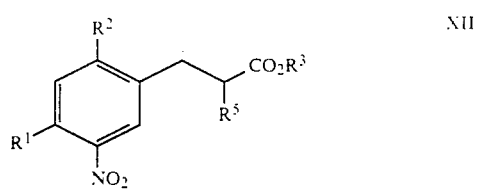
XII compounds of type V being obtained directly;

(c) where $R^4$ is not hydrogen or halogen and $R^5$ is not cyano, $COR^6$ or $CO_2R^7$: by reacting an appropriate benzyl halide II, preferably a chloride or bromide, in the presence of a base, with or without the addition of a catalyst, in an aprotic solvent, with an aldehyde IX by the method stated in Lieb. Ann. Chem. 1979, 1585 to give an aldehyde X, and oxidizing this to the carboxylic acid XI. Esterification gives the desired compounds IV:

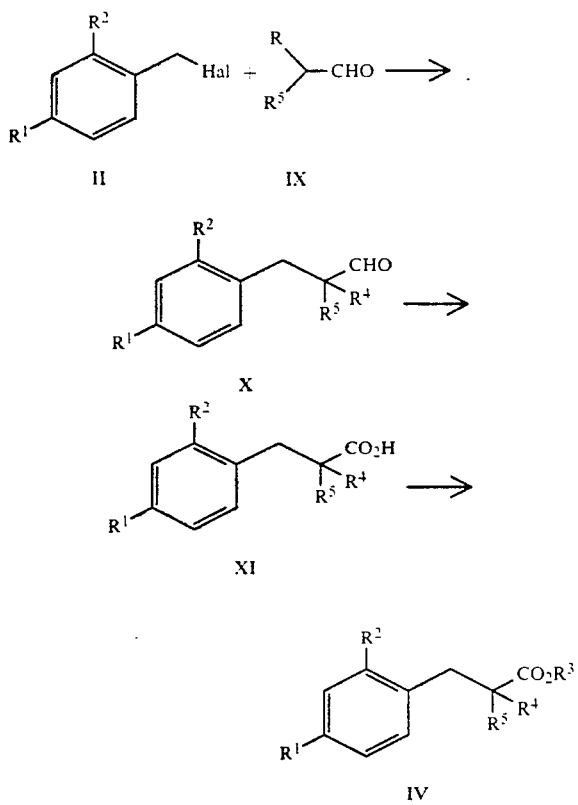

The reaction of II and IX to give X takes place in a two-phase system of, for example, toluene or acetonitrile and an aqueous alkali metal hydroxide in the presence of a quaternary ammonium salt, such as benzyltriethylammonium chloride, tetrabutylammonium iodide, tetrabutylammonium hydroxide or tetrabutylammonium hydrogen sulfate.

The procedures recommended in the Examples below were used with appropriate modification of the starting compounds to obtain further compounds I; the compounds obtained are listed together with physical data in the Tables below; compounds without such data can be obtained from corresponding substances in a similar manner. Because of their close structural relationship with the compounds prepared and investigated, they are expected to have a similar action.

EXAMPLE 1

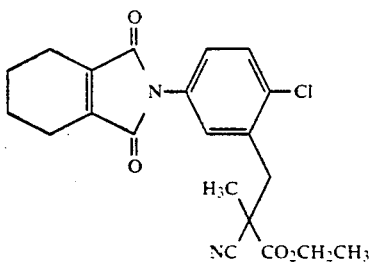

(a) 64.4 g of 2-chlorobenzyl chloride, 76.0 g of ethyl 2-cyanopropionate, 58.0 g of dry potassium carbonate and 0.1 g of 18-crown-6 are refluxed for 3 hours in the absence of moisture. Filtration and distillation of the residue gives 69.5 g of ethyl 2-chlorobenzylmethylcyanoacetate (bp.: 107°–109° C./0.1).

(b) 41.7 ml of concentrated nitric acid (d=1.51) are added to 25.2 g of the ester at from 0° to 5° C. in the course of 30 minutes and stirring is carried out for a further 30 minutes. The mixture is stirred into 400 ml of ice water, and the mixture is extracted with twice 70 ml of toluene. Washing with 10% strength sodium bicarbonate solution and water, evaporation of the solvent and recrystallization from 50 ml of diisopropyl ether gives 18.9 g of ethyl (2-chloro-5-nitrobenzyl)methylcyanoacetate (mp.: 72°–74° C.).

(c) A solution of 18.7 g of the nitro compound in 28 ml of methanol and 40 ml of glacial acetic acid is added dropwise to a mixture of 10.6 g of iron powder in 70 ml of methanol and 15 ml of glacial acetic acid under reflux in the course of 1 hour. After the mixture has been refluxed for a further 30 minutes, the product is filtered off under suction and washed with 50 ml of ethyl acetate. It is stirred into 800 ml of water and the mixture is extracted with three times 100 ml of ethyl acetate. Drying and evaporation of the solvent under reduced pressure gives 15.5 g of ethyl (2-chloro-5-aminobenzyl)-methylcyanoacetate as a liquid (at room temperature).

(d) 15.5 g of the amino compound and 9.3 g of cyclohexene-1,2-dicarboxylic anhydride in 150 ml of glacial acetic acid are stirred for 5 hours at 50° C. The solvent is evaporated under reduced pressure and 14.4 g of ethyl 2-chloro-5-(N-3,4,5,6-tetrahydrophthalimido)-benzylmethylcyanoacetate of melting point 111°–113° C. (active ingredient example 2.020) are obtained from the residue (23.0 g) by recrystallization from 80 ml of methanol.

Further examples of active ingredients, which can be prepared by this synthesis principle, are shown in Tables 2, 3 and 4.

EXAMPLE 2

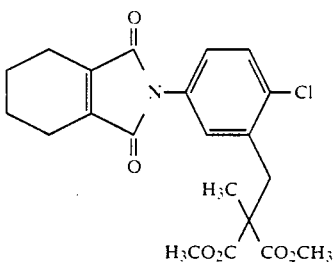

(a) 3 g of sodium hydride (80% strength suspension in linseed oil) in 150 ml of dimethylformamide are initially taken at room temperature in the absence of moisture, and 25.7 g of dimethyl 2-chlorobenzylmalonate (J. Amer. Chem. Soc. 71 (1949), 2644) in 50 ml of dimethylformamide are added dropwise. When evolution of hydrogen is complete, 14.2 g of methyl iodide in 50 ml of dimethylformamide are added and stirring is continued for 16 hours. The mixture is poured onto 300 ml of ice water and crystallized in the cold. The crystals are filtered off under suction and dried to give 23.5 g of dimethyl 2-chlorobenzylmethylmalonate (mp.: 52°–53° C.).

(b) 23.5 g of the diester are nitrated with 36.1 ml of concentrated nitric acid (d=1.51) at 0°–5° C. 23.4 g of dimethyl (2-chloro-5-nitrobenzyl)-methylmalonate are obtained as a liquid (at room temperature) from the toluene phase after washing with 10% strength sodium bicarbonate solution and water and stripping off the solvent under reduced pressure.

(c) 23.4 g of the nitro compound are reduced with 11.1 g of iron powder in a total of 55 ml of glacial acetic acid and 100 ml of methanol. 16.7 g of dimethyl (2-chloro-5-aminobenzyl)-methylmalonate are obtained as a liquid (at room temperature) from the crude product (20.8 g) by extraction with ethyl acetate.

(d) 26.8 g of crude product are obtained from 16.7 g of the amino compound and 10.2 g of cyclohexene-1,2-dicarboxylic anhydride in 250 ml of glacial acetic acid, and the crude product is chromatographed over silica gel with toluene/1% strength acetone to give 13.7 g of dimethyl [2-chloro-5-(N-3,4,5,6-tetrahydrophthalamido)benzyl]-methylmalonate of melting point 103°–105° C. (active ingredient example 3.010).

Further examples of active ingredients which can be prepared by this synthesis principle are shown in Table 3.

EXAMPLE 3

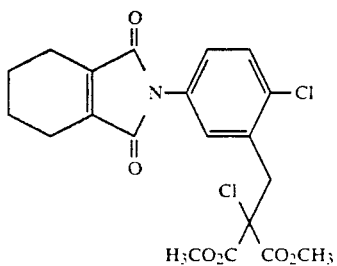

(a) A mixture of 9 ml of concentrated nitric acid (d=1.51) and 20 ml of concentrated sulfuric acid is added dropwise in the course of 1 hour to a stirred solution of 51.3 g of dimethyl 2-chlorobenzylmalonate (J. Amer. Chem. Soc. 71 (1949), 2644) in 80 ml of concentrated sulfuric acid at from 3° to 5° C., and stirring is continued for 2 hours at the same temperature. The mixture is stirred into 1 l of ice water, extracted with twice 100 ml of toluene and washed with 10% strength sodium bicarbonate solution and water, after which 58.3 g of crystalline crude product is isolated. Recrystallization of the crude product from 120 ml of diisopropyl ether gives 40.0 g of dimethyl (2-chloro-5-nitrobenzyl)-malonate of melting point 72°–74° C.

(b) 9.5 g of sulfuryl chloride are added dropwise to a solution of 20.0 g of the nitro compound in 80 ml of glacial acetic acid at from 80° to 85° C. and the mixture is refluxed for 2 hours. After the solvent has been evaporated off, the residue is stirred with 150 ml of water and the product is filtered off under suction and made into a paste with 70 ml of 5% strength sodium bicarbonate solution. 14.9 g of dimethyl (2-chloro-5-nitrobenzyl)-chloromalonate of melting point 75°–78° C. are isolated from the crude product (19.4 g, mp.: 69°–74° C.) by recrystallization from 50 ml of methanol.

(c) 14.9 g of the nitro compound are reduced with 7.5 g of iron powder in a total of 38 ml of glacial acetic acid and 70 ml of methanol. 10.2 g of dimethyl (2-chloro-5-aminobenzyl)-chloromalonate of melting point 107°–109° C. are obtained from the crude product (13.8 g) by making it into a paste with 50 ml of diisopropyl ether.

(d) 15.0 g of crude product are obtained from 10.0 g of the amino compound and 5.2 g of cyclohexene-1,2-dicarboxylic anhydride in 130 ml of glacial acetic acid. Recrystallization of the crude product from 200 ml of methanol gives 9.5 g of dimethyl [2-chloro-5-(N-3,4,5,6-tetrahydrophthalimido)-benzyl]-chloromalonate of melting point 131°–133° C. (active ingredient example 3.002).

Further examples of active ingredients which can be prepared by this synthesis principle are shown in Tables 2 and 3.

EXAMPLE 4

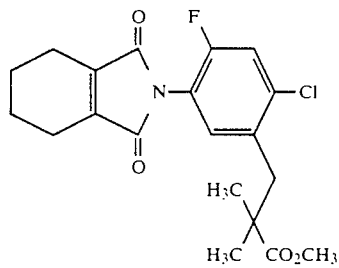

(a) 65.0 g of 2-chloro-4-fluorobenzyl chloride in 90 ml of toluene and 28.8 g of isobutyraldehyde are added dropwise, simultaneously but separately, with thorough mixing at 80° C. in the course of 30 minutes to a mixture of 1.9 g of tetrabutylammonium iodide, 155 g of 30% strength sodium hydroxide solution and 115 ml of toluene, and stirring is continued for 3 hours at 80° C. The organic phase is separated off, washed with three times 50 ml of water, dried, and concentrated (58.5 g) by short-path distillation (bp.=70°–90° C./0.3). Distillation gives 45.1 g of (2-chloro-4-fluorophenyl)-pivalaldehyde (bp.: 53°–55° C./0.1).

(b) 54.5 g of amidosulfonic acid and a solution of 100.1 g of disodium hydrogen phosphate in 200 ml of water are added to a solution of 90.0 g of the above aldehyde in 200 ml of dioxane. a solution of 57.0 g of 80% strength sodium chlorite in 200 ml of water is added dropwise at room temperature in the course of 45 minutes with stirring at a pH of 4 and stirring is continued for 6 hours at the same temperature. The dioxane is stripped off under reduced pressure, the residue is extracted with three times 250 ml of ether, with 100 ml of water and with three times 120 ml of 2N sodium hydroxide solution. The sodium hydroxide extract is washed once with 100 ml of ether, acidified to pH 3 with semiconcentrated hydrochloric acid and then extracted by shaking with three times 250 ml of ether. 74.8 g of 2-chloro-4-fluorophenyl)-pivalic acid of melting point 43°–44° C. are isolated.

(c) 86 g of crude nitro compound are obtained from 74.5 g of the acid in 140 ml of concentrated sulfuric acid and 16.2 ml of nitric acid (d=1.51) in 30 ml of concentrated sulfuric acid. Recrystallization of the said crude compound from 450 ml of cyclohexane gives 70.8 g of (2-chloro-4-fluoro-5-nitrophenyl)-pivalic acid of melting point 102°–104° C.

(d) 5.3 ml of thionyl chloride are added dropwise to 13.2 g of the nitro compound in 130 ml of toluene after the addition of 1 drop of dimethylformamide at 90°–100° C., and stirring is continued at 100°–110° C. until the evolution of gas has ended (about 1 hour). After the solvent has been evaporated under reduced pressure, the residue is taken up with three times 30 ml of toluene and the solution is again evaporated down under reduced pressure. The residue (15.0 g) is taken up in 50 ml of methanol at 10° C., and 6.5 ml of α-picoline are added dropwise at 5° C. The mixture is stirred for 24 hours and then evaporated to dryness, and the residue is taken up with 150 ml of ether and 30 ml of 2N hydrochloric acid. The ether phase is washed with water and dried and the ether is evaporated to give 12.8 g of methyl (2-chloro-4-fluoro-5-nitrophenyl)-pivalate (liquid at room temperature).

(e) 10.8 of methyl (2-chloro-4-fluoro-5-aminophenyl)-pivalate (liquid at room temperature) are obtained from 12.7 g of the nitrated ester and 16.7 g of iron powder in a total of 100 ml of methanol and 55 ml of glacial acetic acid.

(f) 16.0 g of crude product are obtained from 10.6 g of the amino compound and 6.5 g of cyclohexene-1,2-dicarboxylic anhydride in 80 ml of glacial acetic acid. Chromatography over 60 g of silica gel using toluene gives 12.3 g of methyl [2-chloro-4-fluoro-5-(N-3,4,5,6-tetrahydrophthalimido)-phenyl]-pivalate of melting point 68°–70° C. (active ingredient example 1.020).

Further examples of active ingredients which can be prepared by this synthesis principle are shown in Table 1.

TABLE 1

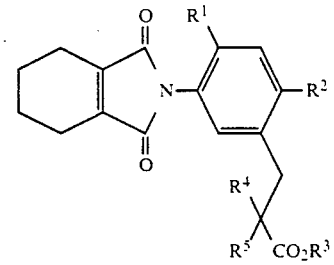

| Nr. | $R^1$ | $R^2$ | $R^3$ | $R^4$ | $R^5$ | M.p. |
|---|---|---|---|---|---|---|
| 1.001 | H | Cl | $CH_3$ | H | $CH_3$ | |
| 1.002 | F | Cl | $CH_3$ | H | $CH_3$ | |
| 1.003 | H | Cl | $CH_2CH_3$ | H | $CH_3$ | |
| 1.004 | F | Cl | $CH_2CH_3$ | H | $CH_3$ | |
| 1.005 | H | Cl | $CH_2CH_2OCH_3$ | H | $CH_3$ | |
| 1.006 | F | Cl | $CH_2CH_2OCH_3$ | H | $CH_3$ | |
| 1.007 | H | Cl | $CH_3$ | H | $CH_2CH_3$ | |
| 1.008 | F | Cl | $CH_3$ | H | $CH_2CH_3$ | |
| 1.009 | H | Cl | $CH_2CH_3$ | H | $CH_2CH_3$ | |
| 1.010 | F | Cl | $CH_2CH_3$ | H | $CH_2CH_3$ | |
| 1.011 | H | Cl | $CH_2CH_2OCH_3$ | H | $CH_2CH_3$ | |
| 1.012 | F | Cl | $CH_2CH_2OCH_3$ | H | $CH_2CH_3$ | |
| 1.013 | H | Cl | $CH_3$ | H | $CH_2CH_2CH_3$ | |
| 1.014 | F | Cl | $CH_3$ | H | $CH_2CH_2CH_3$ | |
| 1.015 | H | Cl | $CH_2CH_3$ | H | $CH_2CH_2CH_3$ | |
| 1.016 | F | Cl | $CH_2CH_3$ | H | $CH_2CH_2CH_3$ | |
| 1.017 | H | Cl | $CH_2CH_2OCH_3$ | H | $CH_2CH_2CH_3$ | |
| 1.018 | F | Cl | $CH_2CH_2OCH_3$ | H | $CH_2CH_2CH_3$ | |
| 1.019 | H | Cl | $CH_3$ | $CH_3$ | $CH_3$ | 103–4° C. |
| 1.020 | F | Cl | $CH_3$ | $CH_3$ | $CH_3$ | 68–70° C. |
| 1.021 | Cl | Cl | $CH_3$ | $CH_3$ | $CH_3$ | 122–3° C. |
| 1.022 | H | Cl | $CH_2CH_3$ | $CH_3$ | $CH_3$ | |
| 1.023 | F | Cl | $CH_2CH_3$ | $CH_3$ | $CH_3$ | oil |
| 1.024 | Cl | Cl | $CH_2CH_3$ | $CH_3$ | $CH_3$ | 88–89° C. |
| 1.025 | H | Cl | $CH_2CH_2CH_2CH_3$ | $CH_3$ | $CH_3$ | |
| 1.026 | F | Cl | $CH_2CH_2CH_2CH_3$ | $CH_3$ | $CH_3$ | |
| 1.027 | Cl | Cl | $CH_2CH_2CH_2CH_3$ | $CH_3$ | $CH_3$ | |
| 1.028 | H | Cl | $CH_2CH_2CH(CH_3)_2$ | $CH_3$ | $CH_3$ | |
| 1.029 | F | Cl | $CH_2CH_2CH(CH_3)_2$ | $CH_3$ | $CH_3$ | 98–99° C. |
| 1.030 | Cl | Cl | $CH_2CH_2CH(CH_3)_2$ | $CH_3$ | $CH_3$ | 112° C. |
| 1.031 | H | Cl | $CH_2CH_2OCH_3$ | $CH_3$ | $CH_3$ | oil |
| 1.032 | F | Cl | $CH_2CH_2OCH_3$ | $CH_3$ | $CH_3$ | oil |
| 1.033 | Cl | Cl | $CH_2CH_2OCH_3$ | $CH_3$ | $CH_3$ | oil |
| 1.034 | H | Cl | $CH_2CH_2OCH_2CH_3$ | $CH_3$ | $CH_3$ | |
| 1.035 | F | Cl | $CH_2CH_2OCH_2CH_3$ | $CH_3$ | $CH_3$ | 63–4° C. |
| 1.036 | Cl | Cl | $CH_2CH_2OCH_2CH_3$ | $CH_3$ | $CH_3$ | oil |
| 1.037 | H | Cl | $CH_2CH_2SCH_2CH_3$ | $CH_3$ | $CH_3$ | |
| 1.038 | F | Cl | $CH_2CH_2SCH_2CH_3$ | $CH_3$ | $CH_3$ | |
| 1.039 | H | Cl | cyclopentyl | $CH_3$ | $CH_3$ | |
| 1.040 | F | Cl | cyclopentyl | $CH_3$ | $CH_3$ | |
| 1.041 | H | Cl | $CH_2CH=CH_2$ | $CH_3$ | $CH_3$ | |
| 1.042 | F | Cl | $CH_2CH=CH_2$ | $CH_3$ | $CH_3$ | |
| 1.043 | H | Cl | $CH_2C\equiv CH$ | $CH_3$ | $CH_3$ | |
| 1.044 | F | Cl | $CH_2C\equiv CH$ | $CH_3$ | $CH_3$ | |
| 1.045 | H | Cl | $CH_3$ | $CH_3$ | $CH_2CH_3$ | |
| 1.046 | F | Cl | $CH_3$ | $CH_3$ | $CH_2CH_3$ | oil |

TABLE 1-continued

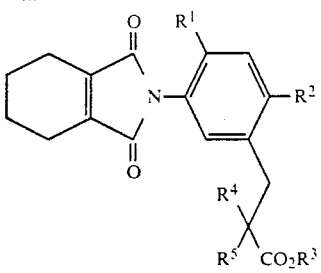

| Nr. | R$^1$ | R$^2$ | R$^3$ | R$^4$ | R$^5$ | M.p. |
|---|---|---|---|---|---|---|
| 1.047 | H | Cl | CH$_2$CH$_3$ | CH$_3$ | CH$_2$CH$_3$ | |
| 1.048 | F | Cl | CH$_2$CH$_3$ | CH$_3$ | CH$_2$CH$_3$ | |
| 1.049 | H | Cl | CH$_2$CH$_2$OCH$_3$ | CH$_3$ | CH$_2$CH$_3$ | |
| 1.050 | F | Cl | CH$_2$CH$_2$OCH$_3$ | CH$_3$ | CH$_2$CH$_3$ | |
| 1.051 | H | Cl | CH$_3$ | CH$_3$ | CH$_2$CH$_2$CH$_3$ | |
| 1.052 | F | Cl | CH$_3$ | CH$_3$ | CH$_2$CH$_2$CH$_3$ | |
| 1.053 | H | Cl | CH$_2$CH$_3$ | CH$_3$ | CH$_2$CH$_2$CH$_3$ | |
| 1.054 | F | Cl | CH$_2$CH$_3$ | CH$_3$ | CH$_2$CH$_2$CH$_3$ | |
| 1.055 | H | Cl | CH$_2$CH$_2$OCH$_3$ | CH$_3$ | CH$_2$CH$_2$CH$_3$ | |
| 1.056 | F | Cl | CH$_2$CH$_2$OCH$_3$ | CH$_3$ | CH$_2$CH$_2$CH$_3$ | |
| 1.057 | H | Cl | CH$_3$ | CH$_2$CH$_3$ | CH$_2$CH$_3$ | 103–105° C. |
| 1.058 | F | Cl | CH$_3$ | CH$_2$CH$_3$ | CH$_2$CH$_3$ | oil |
| 1.059 | H | Cl | CH$_2$CH$_3$ | CH$_2$CH$_3$ | CH$_2$CH$_3$ | |
| 1.060 | F | Cl | CH$_2$CH$_3$ | CH$_2$CH$_3$ | CH$_2$CH$_3$ | |
| 1.061 | H | Cl | CH$_2$CH$_2$OCH$_3$ | CH$_2$CH$_3$ | CH$_2$CH$_3$ | |
| 1.062 | F | Cl | CH$_2$CH$_2$OCH$_3$ | CH$_2$CH$_3$ | CH$_2$CH$_3$ | |
| 1.063 | H | Cl | CH$_3$ | CH$_2$CH$_3$ | CH$_2$CH$_2$CH$_3$ | |
| 1.064 | F | Cl | CH$_3$ | CH$_2$CH$_3$ | CH$_2$CH$_2$CH$_3$ | |
| 1.065 | H | Cl | CH$_2$CH$_3$ | CH$_2$CH$_3$ | CH$_2$CH$_2$CH$_3$ | |
| 1.066 | F | Cl | CH$_2$CH$_3$ | CH$_2$CH$_3$ | CH$_2$CH$_2$CH$_3$ | |
| 1.067 | H | Cl | CH$_2$CH$_2$OCH$_3$ | CH$_2$CH$_3$ | CH$_2$CH$_2$CH$_3$ | |
| 1.068 | F | Cl | CH$_2$CH$_2$OCH$_3$ | CH$_2$CH$_3$ | CH$_2$CH$_2$CH$_3$ | |
| 1.069 | H | Cl | CH$_3$ | CH$_2$CH$_2$CH$_3$ | CH$_2$CH$_2$CH$_3$ | |
| 1.070 | F | Cl | CH$_3$ | CH$_2$CH$_2$CH$_3$ | CH$_2$CH$_2$CH$_3$ | |
| 1.071 | H | Cl | CH$_2$CH$_3$ | CH$_2$CH$_2$CH$_3$ | CH$_2$CH$_2$CH$_3$ | |
| 1.072 | F | Cl | CH$_2$CH$_3$ | CH$_2$CH$_2$CH$_3$ | CH$_2$CH$_2$CH$_3$ | |
| 1.073 | H | Cl | CH$_2$CH$_2$OCH$_3$ | CH$_2$CH$_2$CH$_3$ | CH$_2$CH$_2$CH$_3$ | |
| 1.074 | F | Cl | CH$_2$CH$_2$OCH$_3$ | CH$_2$CH$_2$CH$_3$ | CH$_2$CH$_2$CH$_3$ | |
| 1.075 | H | Cl | CH$_3$ | CH$_2$CH$_2$CH$_2$CH$_2$ | | 108–109° C. |
| 1.076 | F | Cl | CH$_3$ | CH$_2$CH$_2$CH$_2$CH$_2$ | | 65–70° C. |
| 1.077 | H | Cl | CH$_2$CH$_3$ | CH$_2$CH$_2$CH$_2$CH$_2$ | | |
| 1.078 | F | Cl | CH$_2$CH$_3$ | CH$_2$CH$_2$CH$_2$CH$_2$ | | |
| 1.079 | H | Cl | CH$_2$CH$_2$OCH$_3$ | CH$_2$CH$_2$CH$_2$CH$_2$ | | |
| 1.080 | F | Cl | CH$_2$CH$_2$OCH$_3$ | CH$_2$CH$_2$CH$_2$CH$_2$ | | |
| 1.081 | H | Cl | CH$_3$ | CH$_2$CH$_2$CH$_2$CH$_2$CH$_2$ | | |
| 1.082 | F | Cl | CH$_3$ | CH$_2$CH$_2$CH$_2$CH$_2$CH$_2$ | | 131–4° C. |
| 1.083 | H | Cl | CH$_2$CH$_3$ | CH$_2$CH$_2$CH$_2$CH$_2$CH$_2$ | | |
| 1.084 | F | Cl | CH$_2$CH$_3$ | CH$_2$CH$_2$CH$_2$CH$_2$CH$_2$ | | |
| 1.085 | H | Cl | CH$_2$CH$_2$OCH$_3$ | CH$_2$CH$_2$CH$_2$CH$_2$CH$_2$ | | |
| 1.086 | F | Cl | CH$_2$CH$_2$OCH$_3$ | CH$_2$CH$_2$CH$_2$CH$_2$CH$_2$ | | |
| 1.087 | H | Cl | CH$_3$ | CH$_2$CH$_2$OCH$_2$ | | |
| 1.088 | F | Cl | CH$_3$ | CH$_2$CH$_2$OCH$_2$ | | |
| 1.089 | H | Cl | CH$_2$CH$_3$ | CH$_2$CH$_2$OCH$_2$ | | |
| 1.090 | F | Cl | CH$_2$CH$_3$ | CH$_2$CH$_2$OCH$_2$ | | |
| 1.091 | H | Cl | CH$_2$CH$_2$OCH$_3$ | CH$_2$CH$_2$OCH$_2$ | | |
| 1.092 | F | Cl | CH$_2$CH$_2$OCH$_3$ | CH$_2$CH$_2$OCH$_2$ | | |
| 1.093 | H | Cl | CH$_3$ | CH$_2$CH$_2$CH$_2$OCH$_2$ | | |
| 1.094 | F | Cl | CH$_3$ | CH$_2$CH$_2$CH$_2$OCH$_2$ | | |
| 1.095 | H | Cl | CH$_2$CH$_3$ | CH$_2$CH$_2$CH$_2$OCH$_2$ | | |
| 1.096 | F | Cl | CH$_2$CH$_3$ | CH$_2$CH$_2$CH$_2$OCH$_2$ | | |
| 1.097 | H | Cl | CH$_2$CH$_2$OCH$_3$ | CH$_2$CH$_2$CH$_2$OCH$_2$ | | |
| 1.098 | F | Cl | CH$_2$CH$_2$OCH$_3$ | CH$_2$CH$_2$CH$_2$OCH$_2$ | | |
| 1.099 | H | Cl | CH$_3$ | CH$_2$CH$_2$OCH$_2$CH$_2$ | | |
| 1.100 | F | Cl | CH$_3$ | CH$_2$CH$_2$OCH$_2$CH$_2$ | | |
| 1.101 | H | Cl | CH$_2$CH$_3$ | CH$_2$CH$_2$OCH$_2$CH$_2$ | | |
| 1.102 | F | Cl | CH$_2$CH$_3$ | CH$_2$CH$_2$OCH$_2$CH$_2$ | | |
| 1.103 | H | Cl | CH$_2$CH$_2$OCH$_3$ | CH$_2$CH$_2$OCH$_2$CH$_2$ | | |
| 1.104 | F | Cl | CH$_2$CH$_2$OCH$_3$ | CH$_2$CH$_2$OCH$_2$CH$_2$ | | |
| 1.105 | H | Cl | CH$_3$ | CH$_2$CH$_2$SCH$_2$ | | |
| 1.106 | F | Cl | CH$_3$ | CH$_2$CH$_2$SCH$_2$ | | |
| 1.107 | H | Cl | CH$_2$CH$_3$ | CH$_2$CH$_2$SCH$_2$ | | |
| 1.108 | F | Cl | CH$_2$CH$_3$ | CH$_2$CH$_2$SCH$_2$ | | |
| 1.109 | H | Cl | CH$_2$CH$_2$OCH$_3$ | CH$_2$CH$_2$SCH$_2$ | | |
| 1.110 | F | Cl | CH$_2$CH$_2$OCH$_3$ | CH$_2$CH$_2$SCH$_2$ | | |
| 1.111 | H | Cl | CH$_3$ | CH$_2$CH$_2$CH$_2$SCH$_2$ | | |
| 1.112 | F | Cl | CH$_3$ | CH$_2$CH$_2$CH$_2$SCH$_2$ | | |
| 1.113 | H | Cl | CH$_2$CH$_3$ | CH$_2$CH$_2$CH$_2$SCH$_2$ | | |

TABLE 1-continued

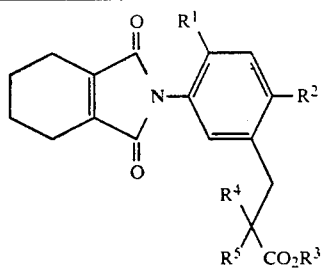

| Nr. | R¹ | R² | R³ | R⁴ | R⁵ | M.p. |
|---|---|---|---|---|---|---|
| 1.114 | F | Cl | CH₂CH₃ | | CH₂CH₂CH₂SCH₂ | |
| 1.115 | H | Cl | CH₂CH₂OCH₃ | | CH₂CH₂CH₂SCH₂ | |
| 1.116 | F | Cl | CH₂CH₂OCH₃ | | CH₂CH₂CH₂SCH₂ | |
| 1.117 | H | Cl | CH₃ | | CH₂CH₂CH₂CO | oil |
| 1.118 | F | Cl | CH₃ | | CH₂CH₂CH₂CO | |
| 1.119 | H | Cl | CH₂CH₃ | | CH₂CH₂CH₂CO | oil |
| 1.120 | F | Cl | CH₂CH₃ | | CH₂CH₂CH₂CO | |
| 1.121 | H | Cl | CH₂CH₂OCH₃ | | CH₂CH₂CH₂CO | |
| 1.122 | F | Cl | CH₂CH₂OCH₃ | | CH₂CH₂CH₂CO | |
| 1.123 | H | Cl | CH₃ | | CH₂CH₂CH₂CH₂CO | |
| 1.124 | F | Cl | CH₃ | | CH₂CH₂CH₂CH₂CO | |
| 1.125 | H | Cl | CH₂CH₃ | | CH₂CH₂CH₂CH₂CO | 138–140° C. |
| 1.126 | F | Cl | CH₂CH₃ | | CH₂CH₂CH₂CH₂CO | |
| 1.127 | H | Cl | CH₂CH₂OCH₃ | | CH₂CH₂CH₂CH₂CO | |
| 1.128 | F | Cl | CH₂CH₂OCH₃ | | CH₂CH₂CH₂CH₂CO | |

TABLE 2

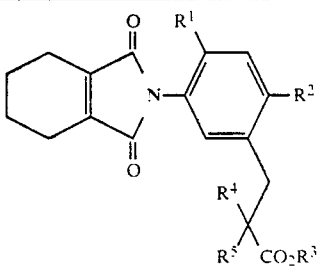

| No. | R¹ | R² | R³ | R⁴ | R⁵ | M.p. |
|---|---|---|---|---|---|---|
| 2.001 | F | Cl | CH₃ | H | CN | |
| 2.002 | H | Cl | CH₂CH₃ | H | CN | |
| 2.003 | F | Cl | CH₂CH₂OCH₃ | H | CN | |
| 2.004 | H | Cl | CH₃ | Cl | CN | |
| 2.005 | F | Cl | CH₃ | Cl | CN | |
| 2.006 | H | Cl | CH₂CH₃ | Cl | CN | |
| 2.007 | F | Cl | CH₂CH₃ | Cl | CN | |
| 2.008 | H | Cl | CH₂CH₂OCH₃ | Cl | CN | |
| 2.009 | F | Cl | CH₂CH₂OCH₃ | Cl | CN | |
| 2.010 | H | Cl | CH₃ | Br | CN | |
| 2.011 | F | Cl | CH₃ | Br | CN | |
| 2.012 | H | Br | CH₃ | Br | CN | |
| 2.013 | F | Br | CH₃ | Br | CN | |
| 2.014 | H | Cl | CH₂CH₃ | Br | CN | |
| 2.015 | F | Cl | CH₂CH₃ | Br | CN | |
| 2.016 | H | Cl | CH₂CH₂OCH₃ | Br | CN | |
| 2.017 | F | Cl | CH₂CH₂OCH₃ | Br | CN | |
| 2.018 | H | Cl | CH₃ | CH₃ | CN | |
| 2.019 | F | Cl | CH₃ | CH₃ | CN | |
| 2.020 | H | Cl | CH₂CH₃ | CH₃ | CN | 111–113° C. |
| 2.021 | F | Cl | CH₂CH₃ | CH₃ | CN | oil |
| 2.022 | H | Cl | CH₂CH₂OCH₃ | CH₃ | CN | |
| 2.023 | F | Cl | CH₂CH₂OCH₃ | CH₃ | CN | |
| 2.024 | H | Cl | CH₃ | CH₂CH₃ | CN | |
| 2.025 | F | Cl | CH₃ | CH₂CH₃ | CN | |
| 2.026 | H | Cl | CH₂CH₃ | CH₂CH₃ | CN | 124–126° C. |
| 2.027 | F | Cl | CH₂CH₃ | CH₂CH₃ | CN | 87–89° C. |
| 2.028 | H | Cl | CH₂CH₂OCH₃ | CH₂CH₃ | CN | |
| 2.029 | F | Cl | CH₂CH₂OCH₃ | CH₂CH₃ | CN | |
| 2.030 | H | Cl | CH₃ | CH₂CH₂CH₃ | CN | |
| 2.031 | F | Cl | CH₃ | CH₂CH₂CH₃ | CN | |
| 2.032 | H | Cl | CH₂CH₃ | CH₂CH₂CH₃ | CN | |
| 2.033 | F | Cl | CH₂CH₃ | CH₂CH₂CH₃ | CN | |

TABLE 2-continued

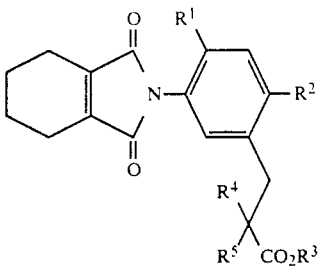

| No. | $R^1$ | $R^2$ | $R^3$ | $R^4$ | $R^5$ | M.p. |
|---|---|---|---|---|---|---|
| 2.034 | H | Cl | $CH_2CH_2OCH_3$ | $CH_2CH_2CH_3$ | CN | |
| 2.035 | F | Cl | $CH_2CH_2OCH_3$ | $CH_2CH_2CH_3$ | CN | |
| 2.036 | H | Cl | $CH_3$ | $CH_2CH_2CH_2CH_3$ | CN | 113–114° C. |
| 2.037 | F | Cl | $CH_3$ | $CH_2CH_2CH_2CH_3$ | CN | 124–125° C. |
| 2.038 | H | Cl | $CH_2CH_3$ | $CH_2CH_2CH_2CH_3$ | CN | |
| 2.039 | F | Cl | $CH_2CH_3$ | $CH_2CH_2CH_2CH_3$ | CN | |
| 2.040 | H | Cl | $CH_2CH_2OCH_3$ | $CH_2CH_2CH_2CH_3$ | CN | |
| 2.041 | F | Cl | $CH_2CH_2OCH_3$ | $CH_2CH_2CH_2CH_3$ | CN | |
| 2.042 | H | Cl | $CH_3$ | H | $COCH_3$ | |
| 2.043 | F | Cl | $CH_3$ | H | $COCH_3$ | |
| 2.044 | H | Cl | $CH_2CH_3$ | H | $COCH_3$ | |
| 2.045 | F | Cl | $CH_2CH_3$ | H | $COCH_3$ | |
| 2.046 | H | Cl | $CH_2CH_2OCH_3$ | H | $COCH_3$ | |
| 2.047 | F | Cl | $CH_2CH_2OCH_3$ | H | $COCH_3$ | |
| 2.048 | H | Cl | $CH_3$ | Cl | $COCH_3$ | |
| 2.049 | F | Cl | $CH_3$ | Cl | $COCH_3$ | |
| 2.050 | H | Cl | $CH_2CH_3$ | Cl | $COCH_3$ | 123–5° C. |
| 2.051 | F | Cl | $CH_2CH_3$ | Cl | $COCH_3$ | |
| 2.052 | H | Cl | $CH_2CH_2OCH_3$ | Cl | $COCH_3$ | |
| 2.053 | F | Cl | $CH_2CH_2OCH_3$ | Cl | $COCH_3$ | |
| 2.054 | H | Cl | $CH_3$ | Br | $COCH_3$ | |
| 2.055 | F | Cl | $CH_3$ | Br | $COCH_3$ | |
| 2.056 | H | Br | $CH_3$ | Br | $COCH_3$ | |
| 2.057 | F | Br | $CH_3$ | Br | $COCH_3$ | |
| 2.058 | H | Cl | $CH_2CH_3$ | Br | $COCH_3$ | |
| 2.059 | F | Cl | $CH_2CH_3$ | Br | $COCH_3$ | |
| 2.060 | H | Cl | $CH_2CH_2OCH_3$ | Br | $COCH_3$ | |
| 2.061 | F | Cl | $CH_2CH_2OCH_3$ | Br | $COCH_3$ | |
| 2.062 | H | Cl | $CH_3$ | $CH_3$ | $COCH_3$ | 108–110° C. |
| 2.063 | F | Cl | $CH_3$ | $CH_3$ | $COCH_3$ | oil |
| 2.064 | H | Cl | $CH_2CH_3$ | $CH_3$ | $COCH_3$ | 103–4° C. |
| 2.065 | F | Cl | $CH_2CH_3$ | $CH_3$ | $COCH_3$ | oil |
| 2.066 | H | Cl | $CH_2CH_2OCH_3$ | $CH_3$ | $COCH_3$ | |
| 2.067 | F | Cl | $CH_2CH_2OCH_3$ | $CH_3$ | $COCH_3$ | |
| 2.068 | H | Cl | $CH_3$ | $CH_2CH_3$ | $COCH_3$ | |
| 2.069 | F | Cl | $CH_3$ | $CH_2CH_3$ | $COCH_3$ | |
| 2.070 | H | Cl | $CH_2CH_3$ | $CH_2CH_3$ | $COCH_3$ | oil |
| 2.071 | F | Cl | $CH_2CH_3$ | $CH_2CH_3$ | $COCH_3$ | oil |
| 2.072 | H | Cl | $CH_2CH_2OCH_3$ | $CH_2CH_3$ | $COCH_3$ | |
| 2.073 | F | Cl | $CH_2CH_2OCH_3$ | $CH_2CH_3$ | $COCH_3$ | |
| 2.074 | H | Cl | $CH_3$ | H | $COCH_2CH_3$ | |
| 2.075 | F | Cl | $CH_3$ | H | $COCH_2CH_3$ | |
| 2.076 | H | Cl | $CH_2CH_3$ | H | $COCH_2CH_3$ | |
| 2.077 | F | Cl | $CH_2CH_3$ | H | $COCH_2CH_3$ | |
| 2.078 | H | Cl | $CH_2CH_2OCH_3$ | H | $COCH_2CH_3$ | |
| 2.079 | F | Cl | $CH_2CH_2OCH_3$ | H | $COCH_2CH_3$ | |
| 2.080 | H | Cl | $CH_3$ | Cl | $COCH_2CH_3$ | |
| 2.081 | F | Cl | $CH_3$ | Cl | $COCH_2CH_3$ | |
| 2.082 | H | Cl | $CH_2CH_3$ | Cl | $COCH_2CH_3$ | |
| 2.083 | F | Cl | $CH_2CH_3$ | Cl | $COCH_2CH_3$ | |
| 2.084 | H | Cl | $CH_2CH_2OCH_3$ | Cl | $COCH_2CH_3$ | |
| 2.085 | F | Cl | $CH_2CH_2OCH_3$ | Cl | $COCH_2CH_3$ | |
| 2.086 | H | Cl | $CH_3$ | Br | $COCH_2CH_3$ | |
| 2.087 | F | Cl | $CH_3$ | Br | $COCH_2CH_3$ | |
| 2.088 | H | Br | $CH_3$ | Br | $COCH_2CH_3$ | |
| 2.089 | F | Br | $CH_3$ | Br | $COCH_2CH_3$ | |
| 2.090 | H | Cl | $CH_2CH_3$ | Br | $COCH_2CH_3$ | |
| 2.091 | F | Cl | $CH_2CH_3$ | Br | $COCH_2CH_3$ | |
| 2.092 | H | Cl | $CH_2CH_2OCH_3$ | Br | $COCH_2CH_3$ | |
| 2.093 | F | Cl | $CH_2CH_2OCH_3$ | Br | $COCH_2CH_3$ | |
| 2.094 | H | Cl | $CH_3$ | $CH_3$ | $COCH_2CH_3$ | |
| 2.095 | F | Cl | $CH_3$ | $CH_3$ | $COCH_2CH_3$ | |
| 2.096 | H | Cl | $CH_2CH_3$ | $CH_3$ | $COCH_2CH_3$ | |
| 2.097 | F | Cl | $CH_2CH_3$ | $CH_3$ | $COCH_2CH_3$ | |
| 2.098 | H | Cl | $CH_2CH_2OCH_3$ | $CH_3$ | $COCH_2CH_3$ | |
| 2.099 | F | Cl | $CH_2CH_2OCH_3$ | $CH_3$ | $COCH_2CH_3$ | |
| 2.100 | H | Cl | $CH_3$ | $CH_2CH_3$ | $COCH_2CH_3$ | |

TABLE 2-continued

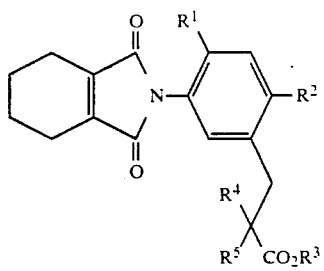

| No. | R¹ | R² | R³ | R⁴ | R⁵ | M.p. |
|---|---|---|---|---|---|---|
| 2.101 | F | Cl | $CH_3$ | $CH_2CH_3$ | $COCH_2CH_3$ | |
| 2.102 | H | Cl | $CH_2CH_3$ | $CH_2CH_3$ | $COCH_2CH_3$ | |
| 2.103 | F | Cl | $CH_2CH_3$ | $CH_2CH_3$ | $COCH_2CH_3$ | |
| 2.104 | H | Cl | $CH_2CH_2OCH_3$ | $CH_2CH_3$ | $COCH_2CH_3$ | |
| 2.105 | F | Cl | $CH_2CH_2OCH_3$ | $CH_2CH_3$ | $COCH_2CH_3$ | |
| 2.106 | H | Cl | $CH_3$ | $CH_2CH_2CH_3$ | $COCH_3$ | |
| 2.107 | F | Cl | $CH_3$ | $CH_2CH_2CH_3$ | $COCH_3$ | |
| 2.108 | H | Cl | $CH_3$ | $CH_2CH_2CH_2CH_3$ | $COCH_3$ | 117–119° C. |
| 2.109 | F | Cl | $CH_3$ | $CH_2CH_2CH_2CH_3$ | $COCH_3$ | 84–86° C. |
| 2.110 | H | Cl | $CH_3$ | $CH_3$ | $COCH(CH_3)_2$ | 120–122° C. |
| 2.111 | F | Cl | $CH_3$ | $CH_3$ | $COCH(CH_3)_2$ | oil |

TABLE 3

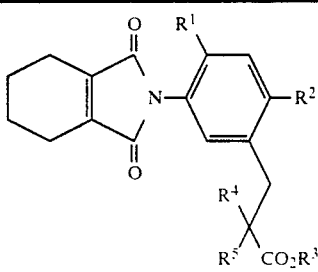

| No. | R¹ | R² | R³ | R⁴ | R⁵ | M.p. |
|---|---|---|---|---|---|---|
| 3.001 | F | Cl | $CH_3$ | H | $CO_2CH_3$ | 115–117° C. |
| 3.002 | H | Cl | $CH_3$ | Cl | $CO_2CH_3$ | 131–133° C. |
| 3.003 | F | Cl | $CH_3$ | Cl | $CO_2CH_3$ | 122–124° C. |
| 3.004 | H | Br | $CH_3$ | Cl | $CO_2CH_3$ | |
| 3.005 | F | Br | $CH_3$ | Cl | $CO_2CH_3$ | |
| 3.006 | H | Br | $CH_3$ | Br | $CO_2CH_3$ | |
| 3.007 | F | Br | $CH_3$ | Br | $CO_2CH_3$ | |
| 3.008 | H | Cl | $CH_3$ | Br | $CO_2CH_3$ | 102–106° C. |
| 3.009 | F | Cl | $CH_3$ | Br | $CO_2CH_3$ | |
| 3.010 | H | Cl | $CH_3$ | $CH_3$ | $CO_2CH_3$ | 103–105° C. |
| 3.011 | F | Cl | $CH_3$ | $CH_3$ | $CO_2CH_3$ | |
| 3.012 | H | Cl | $CH_3$ | $CH_2CH_3$ | $CO_2CH_3$ | |
| 3.013 | F | Cl | $CH_3$ | $CH_2CH_3$ | $CO_2CH_3$ | |
| 3.014 | H | Cl | $CH_3$ | $CH_2CH_2CH_3$ | $CO_2CH_3$ | 128–130° C. |
| 3.015 | F | Cl | $CH_3$ | $CH_2CH_2CH_3$ | $CO_2CH_3$ | |
| 3.016 | H | Cl | $CH_3$ | $CH_2CH(CH_3)_2$ | $CO_2CH_3$ | |
| 3.017 | F | Cl | $CH_3$ | $CH_2CH(CH_3)_2$ | $CO_2CH_3$ | |
| 3.018 | H | Cl | $CH_3$ | 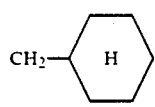 | $CO_2CH_3$ | oil |
| 3.019 | F | Cl | $CH_3$ | 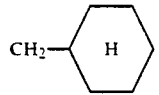 | $CO_2CH_3$ | |
| 3.020 | H | Cl | $CH_3$ |  | $CO_2CH_3$ | |

TABLE 3-continued

| No. | R¹ | R² | R³ | R⁴ | R⁵ | M.p. |
|---|---|---|---|---|---|---|
| 3.021 | F | Cl | $CH_3$ | 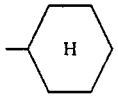 | $CO_2CH_3$ | |
| 3.022 | H | Cl | $CH_3$ | 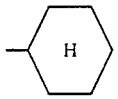 | $CO_2CH_3$ | |
| 3.023 | F | Cl | $CH_3$ | 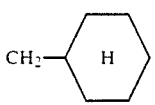 | $CO_2CH_3$ | |
| 3.024 | H | Cl | $CH_3$ | $CH_2CH=CH_2$ | $CO_2CH_3$ | 108-110° C. |
| 3.025 | F | Cl | $CH_3$ | $CH_2CH=CH_2$ | $CO_2CH_3$ | |
| 3.026 | H | Cl | $CH_3$ | $CH_2CH=CHCH_3$ | $CO_2CH_3$ | 90-93° C. |
| 3.027 | F | Cl | $CH_3$ | $CH_2CH=CHCH_3$ | $CO_2CH_3$ | |
| 3.028 | H | Cl | $CH_3$ | $CH_2CH_2CH=CH_2$ | $CO_2CH_3$ | 100-102° C. |
| 3.029 | F | Cl | $CH_3$ | $CH_2CH_2CH=CH_2$ | $CO_2CH_3$ | |
| 3.030 | H | Cl | $CH_3$ | $CH_2C{\equiv}CH$ | $CO_2CH_3$ | 133-135° C. |
| 3.031 | F | Cl | $CH_3$ | $CH_2C{\equiv}CH$ | $CO_2CH_3$ | |
| 3.032 | H | Cl | $CH_3$ | $CH_2C{\equiv}CCH_3$ | $CO_2CH_3$ | |
| 3.033 | F | Cl | $CH_3$ | $CH_2C{\equiv}CCH_3$ | $CO_2CH_3$ | |
| 3.034 | H | Cl | $CH_3$ | $CH_2CH_2OCH_3$ | $CO_2CH_3$ | oil |
| 3.035 | F | Cl | $CH_3$ | $CH_2CH_2OCH_3$ | $CO_2CH_3$ | |
| 3.036 | H | Cl | $CH_3$ | $CH_2CH_2OCH_2CH_3$ | $CO_2CH_3$ | oil |
| 3.037 | F | Cl | $CH_3$ | $CH_2CH_2OCH_2CH_3$ | $CO_2CH_3$ | |
| 3.038 | H | Cl | $CH_3$ | $CH_2CH_2SCH_3$ | $CO_2CH_3$ | |
| 3.039 | F | Cl | $CH_3$ | $CH_2CH_2SCH_3$ | $CO_2CH_3$ | |
| 3.040 | H | Cl | $CH_3$ | $CH_2CH_2SCH_2CH_3$ | $CO_2CH_3$ | |
| 3.041 | F | Cl | $CH_3$ | $CH_2CH_2SCH_2CH_3$ | $CO_2CH_3$ | |
| 3.042 | F | Cl | $CH_2CH_3$ | H | $CO_2CH_2CH_3$ | 89-91° C. |
| 3.043 | H | Cl | $CH_2CH_3$ | Cl | $CO_2CH_2CH_3$ | |
| 3.044 | F | Cl | $CH_2CH_3$ | Cl | $CO_2CH_2CH_3$ | |
| 3.045 | H | Br | $CH_2CH_3$ | Cl | $CO_2CH_2CH_3$ | |
| 3.046 | F | Br | $CH_2CH_3$ | Cl | $CO_2CH_2CH_3$ | |
| 3.047 | H | Br | $CH_2CH_3$ | Br | $CO_2CH_2CH_3$ | |
| 3.048 | F | Br | $CH_2CH_3$ | Br | $CO_2CH_2CH_3$ | |
| 3.049 | H | Cl | $CH_2CH_3$ | Br | $CO_2CH_2CH_3$ | |
| 3.050 | F | Cl | $CH_2CH_3$ | Br | $CO_2CH_2CH_3$ | |
| 3.051 | H | Cl | $CH_2CH_3$ | $CH_3$ | $CO_2CH_2CH_3$ | |
| 3.052 | F | Cl | $CH_2CH_3$ | $CH_3$ | $CO_2CH_2CH_3$ | |
| 3.053 | H | Cl | $CH_2CH_3$ | $CH_2CH_3$ | $CO_2CH_2CH_3$ | |
| 3.054 | F | Cl | $CH_2CH_3$ | $CH_2CH_3$ | $CO_2CH_2CH_3$ | |
| 3.055 | H | Cl | $CH_2CH_3$ | $CH_2CH_2CH_3$ | $CO_2CH_2CH_3$ | |
| 3.056 | F | Cl | $CH_2CH_3$ | $CH_2CH_2CH_3$ | $CO_2CH_2CH_3$ | |
| 3.057 | H | Cl | $CH_2CH_3$ | $CH_2CH(CH_3)_2$ | $CO_2CH_2CH_3$ | |
| 3.058 | F | Cl | $CH_2CH_3$ | $CH_2CH(CH_3)_2$ | $CO_2CH_2CH_3$ | |
| 3.059 | H | Cl | $CH_2CH_3$ | 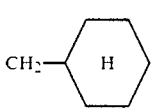 | $CO_2CH_2CH_3$ | |
| 3.060 | F | Cl | $CH_2CH_3$ | 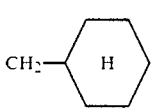 | $CO_2CH_2CH_3$ | |

TABLE 3-continued

| No. | R¹ | R² | R³ | R⁴ | R⁵ | M.p. |
|---|---|---|---|---|---|---|
| 3.061 | H | Cl | CH₂CH₃ |  | CO₂CH₂CH₃ | |
| 3.062 | F | Cl | CH₂CH₃ |  | CO₂CH₂CH₃ | |
| 3.063 | H | Cl | CH₂CH₃ |  | CO₂CH₂CH₃ | |
| 3.064 | F | Cl | CH₂CH₃ |  | CO₂CH₂CH₃ | |
| 3.065 | H | Cl | CH₂CH₃ | CH₂CH=CH₂ | CO₂CH₂CH₃ | |
| 3.066 | F | Cl | CH₂CH₃ | CH₂CH=CH₂ | CO₂CH₂CH₃ | |
| 3.067 | H | Cl | CH₂CH₃ | CH₂CH=CHCH₃ | CO₂CH₂CH₃ | |
| 3.068 | F | Cl | CH₂CH₃ | CH₂CH=CHCH₃ | CO₂CH₂CH₃ | |
| 3.069 | H | Cl | CH₂CH₃ | CH₂CH₂CH=CH₂ | CO₂CH₂CH₃ | |
| 3.070 | F | Cl | CH₂CH₃ | CH₂CH₂CH=CH₂ | CO₂CH₂CH₃ | |
| 3.071 | H | Cl | CH₂CH₃ | CH₂C≡CH | CO₂CH₂CH₃ | |
| 3.072 | F | Cl | CH₂CH₃ | CH₂C≡CH | CO₂CH₂CH₃ | |
| 3.073 | H | Cl | CH₂CH₃ | CH₂C≡CCH₃ | CO₂CH₂CH₃ | |
| 3.074 | F | Cl | CH₂CH₃ | CH₂C≡CCH₃ | CO₂CH₂CH₃ | |
| 3.075 | H | Cl | CH₂CH₃ | CH₂CH₂OCH₃ | CO₂CH₂CH₃ | |
| 3.076 | F | Cl | CH₂CH₃ | CH₂CH₂OCH₃ | CO₂CH₂CH₃ | |
| 3.077 | H | Cl | CH₂CH₃ | CH₂CH₂OCH₂CH₃ | CO₂CH₂CH₃ | |
| 3.078 | F | Cl | CH₂CH₃ | CH₂CH₂OCH₂CH₃ | CO₂CH₂CH₃ | |
| 3.079 | H | Cl | CH₂CH₃ | CH₂CH₂SCH₃ | CO₂CH₂CH₃ | |
| 3.080 | F | Cl | CH₂CH₃ | CH₂CH₂SCH₃ | CO₂CH₂CH₃ | |
| 3.081 | H | Cl | CH₂CH₃ | CH₂CH₂SCH₂CH₃ | CO₂CH₂CH₃ | |
| 3.082 | F | Cl | CH₂CH₃ | CH₂CH₂SCH₂CH₃ | CO₂CH₂CH₃ | |
| 3.083 | F | Cl | CH₂CH₂CH₃ | H | CO₂CH₂CH₂CH₃ | |
| 3.084 | H | Cl | CH₂CH₂CH₃ | Cl | CO₂CH₂CH₂CH₃ | |
| 3.085 | F | Cl | CH₂CH₂CH₃ | Cl | CO₂CH₂CH₂CH₃ | |
| 3.086 | H | Br | CH₂CH₂CH₃ | Cl | CO₂CH₂CH₂CH₃ | |
| 3.087 | F | Br | CH₂CH₂CH₃ | Cl | CO₂CH₂CH₂CH₃ | |
| 3.088 | H | Br | CH₂CH₂CH₃ | Br | CO₂CH₂CH₂CH₃ | |
| 3.089 | F | Br | CH₂CH₂CH₃ | Br | CO₂CH₂CH₂CH₃ | |
| 3.090 | H | Cl | CH₂CH₂CH₃ | Br | CO₂CH₂CH₂CH₃ | |
| 3.091 | F | Cl | CH₂CH₂CH₃ | Br | CO₂CH₂CH₂CH₃ | |
| 3.092 | H | Cl | CH₂CH₂CH₃ | CH₃ | CO₂CH₂CH₂CH₃ | |
| 3.093 | F | Cl | CH₂CH₂CH₃ | CH₃ | CO₂CH₂CH₂CH₃ | |
| 3.094 | H | Cl | CH₂CH₂CH₃ | CH₂CH₃ | CO₂CH₂CH₂CH₃ | |
| 3.095 | F | Cl | CH₂CH₂CH₃ | CH₂CH₃ | CO₂CH₂CH₂CH₃ | |
| 3.096 | H | Cl | CH₂CH₂CH₃ | CH₂CH₂CH₃ | CO₂CH₂CH₂CH₃ | |
| 3.097 | F | Cl | CH₂CH₂CH₃ | CH₂CH₂CH₃ | CO₂CH₂CH₂CH₃ | |
| 3.098 | H | Cl | CH₂CH₂CH₃ | CH₂CH(CH₃)₂ | CO₂CH₂CH₂CH₃ | |
| 3.099 | F | Cl | CH₂CH₂CH₃ | CH₂CH(CH₃)₂ | CO₂CH₂CH₂CH₃ | |
| 3.100 | H | Cl | CH₂CH₂CH₃ | 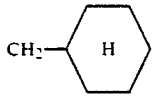 | CO₂CH₂CH₂CH₃ | |

TABLE 3-continued

[Structure: tetrahydroisoindole-1,3-dione with N-attached phenyl bearing R¹ (ortho), R² (para), and a CH₂-C(R⁴)(R⁵)-CO₂R³ group]

| No. | R¹ | R² | R³ | R⁴ | R⁵ | M.p. |
|---|---|---|---|---|---|---|
| 3.101 | F | Cl | $CH_2CH_2CH_3$ | $CH_2$-cyclohexyl(H) | $CO_2CH_2CH_2CH_3$ | |
| 3.102 | H | Cl | $CH_2CH_2CH_3$ | cyclopentyl | $CO_2CH_2CH_2CH_3$ | |
| 3.103 | F | Cl | $CH_2CH_2CH_3$ | cyclopentyl | $CO_2CH_2CH_2CH_3$ | |
| 3.104 | H | Cl | $CH_2CH_2CH_3$ | cyclohexyl(H) | $CO_2CH_2CH_2CH_3$ | |
| 3.105 | F | Cl | $CH_2CH_2CH_3$ | cyclohexyl(H) | $CO_2CH_2CH_2CH_3$ | |
| 3.106 | H | Cl | $CH_2CH_2CH_3$ | $CH_2CH=CH_2$ | $CO_2CH_2CH_2CH_3$ | |
| 3.107 | F | Cl | $CH_2CH_2CH_3$ | $CH_2CH=CH_2$ | $CO_2CH_2CH_2CH_3$ | |
| 3.108 | H | Cl | $CH_2CH_2CH_3$ | $CH_2CH=CHCH_3$ | $CO_2CH_2CH_2CH_3$ | |
| 3.109 | F | Cl | $CH_2CH_2CH_3$ | $CH_2CH=CHCH_3$ | $CO_2CH_2CH_2CH_3$ | |
| 3.110 | H | Cl | $CH_2CH_2CH_3$ | $CH_2CH_2CH=CH_2$ | $CO_2CH_2CH_2CH_3$ | |
| 3.111 | F | Cl | $CH_2CH_2CH_3$ | $CH_2CH_2CH=CH_2$ | $CO_2CH_2CH_2CH_3$ | |
| 3.112 | H | Cl | $CH_2CH_2CH_3$ | $CH_2C{\equiv}CH$ | $CO_2CH_2CH_2CH_3$ | |
| 3.113 | F | Cl | $CH_2CH_2CH_3$ | $CH_2C{\equiv}CH$ | $CO_2CH_2CH_2CH_3$ | |
| 3.114 | H | Cl | $CH_2CH_2CH_3$ | $CH_2C{\equiv}CCH_3$ | $CO_2CH_2CH_2CH_3$ | |
| 3.115 | F | Cl | $CH_2CH_2CH_3$ | $CH_2C{\equiv}CCH_3$ | $CO_2CH_2CH_2CH_3$ | |
| 3.116 | H | Cl | $CH_2CH_2CH_3$ | $CH_2CH_2OCH_3$ | $CO_2CH_2CH_2CH_3$ | |
| 3.117 | F | Cl | $CH_2CH_2CH_3$ | $CH_2CH_2OCH_3$ | $CO_2CH_2CH_2CH_3$ | |
| 3.118 | H | Cl | $CH_2CH_2CH_3$ | $CH_2CH_2OCH_2CH_3$ | $CO_2CH_2CH_2CH_3$ | |
| 3.119 | F | Cl | $CH_2CH_2CH_3$ | $CH_2CH_2OCH_2CH_3$ | $CO_2CH_2CH_2CH_3$ | |
| 3.120 | H | Cl | $CH_2CH_2CH_3$ | $CH_2CH_2SCH_3$ | $CO_2CH_2CH_2CH_3$ | |
| 3.121 | F | Cl | $CH_2CH_2CH_3$ | $CH_2CH_2SCH_3$ | $CO_2CH_2CH_2CH_3$ | |
| 3.122 | H | Cl | $CH_2CH_2CH_3$ | $CH_2CH_2SCH_2CH_3$ | $CO_2CH_2CH_2CH_3$ | |
| 3.123 | F | Cl | $CH_2CH_2CH_3$ | $CH_2CH_2SCH_2CH_3$ | $CO_2CH_2CH_2CH_3$ | |
| 3.124 | H | Cl | $CH_3$ | $CH(CH_3)_2$ | $CO_2CH_3$ | |
| 3.125 | F | Cl | $CH_3$ | $CH(CH_3)_2$ | $CO_2CH_3$ | |
| 3.126 | H | Cl | $CH_3$ | $CH_2CH_2CH_2CH_3$ | $CO_2CH_3$ | 99–101° C. |
| 3.127 | F | Cl | $CH_3$ | $CH_2CH_2CH_2CH_3$ | $CO_2CH_3$ | |
| 3.128 | H | Cl | $CH_3$ | $CH_2SCH_3$ | $CO_2CH_3$ | 130–133° C. |
| 3.129 | F | Cl | $CH_3$ | $CH_2SCH_3$ | $CO_2CH_3$ | |

TABLE 4

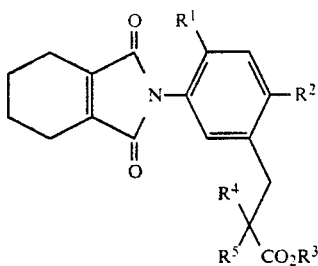

| No. | R¹ | R² | R³ | R⁴ | R⁵ | M.p. |
|---|---|---|---|---|---|---|
| 4.001 | H | Cl | | CH₂CH₂ | CN | |
| 4.002 | F | Cl | | CH₂CH₂ | CN | |
| 4.003 | H | Cl | | CH₂CH₂CH₂ | CN | |
| 4.004 | F | Cl | | CH₂CH₂CH₂ | CN | |
| 4.005 | H | Cl | | CH₂CH₂CH₂CH₂ | CN | |
| 4.006 | F | Cl | | CH₂CH₂CH₂CH₂ | CN | |
| 4.007 | H | Cl | | CH₂CH₂ | CO₂CH₃ | |
| 4.008 | F | Cl | | CH₂CH₂ | CO₂CH₃ | |
| 4.009 | H | Cl | | CH₂CH₂CH₂ | CO₂CH₃ | |
| 4.010 | F | Cl | | CH₂CH₂CH₂ | CO₂CH₃ | |
| 4.011 | H | Cl | | CH₂CH₂CH₂CH₂ | CO₂CH₃ | |
| 4.012 | F | Cl | | CH₂CH₂CH₂CH₂ | CO₂CH₃ | |
| 4.013 | H | Cl | | CH₂CH₂ | CO₂CH₂CH₃ | |
| 4.014 | F | Cl | | CH₂CH₂ | CO₂CH₂CH₃ | |
| 4.015 | H | Cl | | CH₂CH₂CH₂ | CO₂CH₂CH₃ | |
| 4.016 | F | Cl | | CH₂CH₂CH₂ | CO₂CH₂CH₃ | |
| 4.017 | H | Cl | | CH₂CH₂CH₂CH₂ | CO₂CH₂CH₃ | |
| 4.018 | F | Cl | | CH₂CH₂CH₂CH₂ | CO₂CH₂CH₃ | |
| 4.019 | H | Cl | | CH₂CH₂ | CO₂CH₂CH₂OCH₃ | |
| 4.020 | F | Cl | | CH₂CH₂ | CO₂CH₂CH₂OCH₃ | |
| 4.021 | H | Cl | | CH₂CH₂CH₂ | CO₂CH₂CH₂OCH₃ | |
| 4.022 | F | Cl | | CH₂CH₂CH₂ | CO₂CH₂CH₂OCH₃ | |
| 4.023 | H | Cl | | CH₂CH₂CH₂CH₂ | CO₂CH₂CH₂OCH₃ | |
| 4.024 | F | Cl | | CH₂CH₂CH₂CH₂ | CO₂CH₂CH₂OCH₃ | |
| 4.025 | H | Cl | | CH₂CH₂ | COCH₃ | 167–169° C. |
| 4.026 | F | Cl | | CH₂CH₂ | COCH₃ | |
| 4.027 | H | Cl | | CH₂CH₂CH₂ | COCH₃ | |
| 4.028 | F | Cl | | CH₂CH₂CH₂ | COCH₃ | |
| 4.029 | H | Cl | | CH₂CH₂CH₂CH₂ | COCH₃ | |
| 4.030 | F | Cl | | CH₂CH₂CH₂CH₂ | COCH₃ | |
| 4.031 | H | Cl | | CH₂CH₂ | COCH₂CH₃ | 106–108° C. |
| 4.032 | F | Cl | | CH₂CH₂ | COCH₂CH₃ | |
| 4.033 | H | Cl | | CH₂CH₂CH₂ | COCH₂CH₃ | |
| 4.034 | F | Cl | | CH₂CH₂CH₂ | COCH₂CH₃ | |
| 4.035 | H | Cl | | CH₂CH₂CH₂CH₂ | COCH₂CH₃ | |
| 4.036 | F | Cl | | CH₂CH₂CH₂CH₂ | COCH₂CH₃ | |
| 4.037 | H | Cl | | CH₂CH₂ | CH₃ | |
| 4.038 | F | Cl | | CH₂CH₂ | CH₃ | |
| 4.039 | H | Cl | | CH₂CH₂CH₂ | CH₃ | |
| 4.040 | F | Cl | | CH₂CH₂CH₂ | CH₃ | |
| 4.041 | H | Cl | | CH₂CH₂CH₂CH₂ | CH₃ | |
| 4.042 | F | Cl | | CH₂CH₂CH₂CH₂ | CH₃ | |
| 4.043 | H | Cl | | CH₂CH₂ | CH₂CH₃ | |
| 4.044 | F | Cl | | CH₂CH₂ | CH₂CH₃ | |
| 4.045 | H | Cl | | CH₂CH₂CH₂ | CH₂CH₃ | |
| 4.046 | F | Cl | | CH₂CH₂CH₂ | CH₂CH₃ | |
| 4.047 | H | Cl | | CH₂CH₂CH₂CH₂ | CH₂CH₃ | |
| 4.048 | F | Cl | | CH₂CH₂CH₂CH₂ | CH₂CH₃ | |
| 4.049 | H | Cl | | CH₂CH₂ | CH₂CH₂CH₃ | |
| 4.050 | F | Cl | | CH₂CH₂ | CH₂CH₂CH₃ | |
| 4.051 | H | Cl | | CH₂CH₂CH₂ | CH₂CH₂CH₃ | |
| 4.052 | F | Cl | | CH₂CH₂CH₂ | CH₂CH₂CH₃ | |
| 4.053 | H | Cl | | CH₂CH₂CH₂CH₂ | CH₂CH₂CH₃ | |
| 4.054 | F | Cl | | CH₂CH₂CH₂CH₂ | CH₂CH₂CH₃ | |
| 4.055 | H | Cl | | CH₂CH₂ | CH₂CH₂OCH₃ | |
| 4.056 | F | Cl | | CH₂CH₂ | CH₂CH₂OCH₃ | |
| 4.057 | H | Cl | | CH₂CH₂CH₂ | CH₂CH₂OCH₃ | |
| 4.058 | F | Cl | | CH₂CH₂CH₂ | CH₂CH₂OCH₃ | |
| 4.059 | H | Cl | | CH₂CH₂CH₂CH₂ | CH₂CH₂OCH₃ | |
| 4.060 | F | Cl | | CH₂CH₂CH₂CH₂ | CH₂CH₂OCH₃ | |
| 4.061 | H | Cl | | CH₂CH₂ | CH₂CH₂OCH₂CH₃ | |
| 4.062 | F | Cl | | CH₂CH₂ | CH₂CH₂OCH₂CH₃ | |
| 4.063 | H | Cl | | CH₂CH₂CH₂ | CH₂CH₂OCH₂CH₃ | |
| 4.064 | F | Cl | | CH₂CH₂CH₂ | CH₂CH₂OCH₂CH₃ | |
| 4.065 | H | Cl | | CH₂CH₂CH₂CH₂ | CH₂CH₂OCH₂CH₃ | |
| 4.066 | F | Cl | | CH₂CH₂CH₂CH₂ | CH₂CH₂OCH₂CH₃ | |
| 4.067 | H | Cl | | CH₂CH₂ | CH₂CH₂SCH₃ | |

TABLE 4-continued

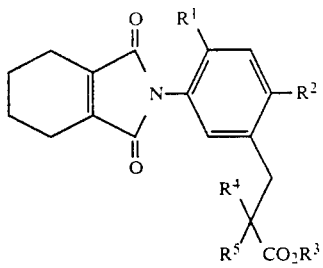

| No. | R$^1$ | R$^2$ | R$^3$ | R$^4$ | R$^5$ | M.p. |
|---|---|---|---|---|---|---|
| 4.068 | F | Cl | | CH$_2$CH$_2$ | CH$_2$CH$_2$SCH$_3$ | |
| 4.069 | H | Cl | | CH$_2$CH$_2$CH$_2$ | CH$_2$CH$_2$SCH$_3$ | |
| 4.070 | F | Cl | | CH$_2$CH$_2$CH$_2$ | CH$_2$CH$_2$SCH$_3$ | |
| 4.071 | H | Cl | | CH$_2$CH$_2$CH$_2$CH$_2$ | CH$_2$CH$_2$SCH$_3$ | |
| 4.072 | F | Cl | | CH$_2$CH$_2$CH$_2$CH$_2$ | CH$_2$CH$_2$SCH$_3$ | |
| 4.073 | H | Cl | | CH$_2$CH$_2$ | CH$_2$CH=CH$_2$ | |
| 4.074 | F | Cl | | CH$_2$CH$_2$ | CH$_2$CH=CH$_2$ | |
| 4.075 | H | Cl | | CH$_2$CH$_2$CH$_2$ | CH$_2$CH=CH$_2$ | |
| 4.076 | F | Cl | | CH$_2$CH$_2$CH$_2$ | CH$_2$CH=CH$_2$ | |
| 4.077 | H | Cl | | CH$_2$CH$_2$CH$_2$CH$_2$ | CH$_2$CH=CH$_2$ | |
| 4.078 | F | Cl | | CH$_2$CH$_2$CH$_2$CH$_2$ | CH$_2$CH=CH$_2$ | |
| 4.079 | H | Cl | | CH$_2$CH$_2$ | CH$_2$CH=CHCH$_3$ | |
| 4.080 | F | Cl | | CH$_2$CH$_2$ | CH$_2$CH=CHCH$_3$ | |
| 4.081 | H | Cl | | CH$_2$CH$_2$CH$_2$ | CH$_2$CH=CHCH$_3$ | |
| 4.082 | F | Cl | | CH$_2$CH$_2$CH$_2$ | CH$_2$CH=CHCH$_3$ | |
| 4.083 | H | Cl | | CH$_2$CH$_2$CH$_2$CH$_2$ | CH$_2$CH=CHCH$_3$ | |
| 4.084 | F | Cl | | CH$_2$CH$_2$CH$_2$CH$_2$ | CH$_2$CH=CHCH$_3$ | |
| 4.085 | H | Cl | | CH$_2$CH$_2$ | CH$_2$C≡CH | |
| 4.086 | F | Cl | | CH$_2$CH$_2$ | CH$_2$C≡CH | |
| 4.087 | H | Cl | | CH$_2$CH$_2$CH$_2$ | CH$_2$C≡CH | |
| 4.088 | F | Cl | | CH$_2$CH$_2$CH$_2$ | CH$_2$C≡CH | |
| 4.089 | H | Cl | | CH$_2$CH$_2$CH$_2$CH$_2$ | CH$_2$C≡CH | |
| 4.090 | F | Cl | | CH$_2$CH$_2$CH$_2$CH$_2$ | CH$_2$C≡CH | |

As stated at the outset, the compounds of the formula I have a herbicidal action and are selective in crop plants.

The active ingredients, or herbicidal agents containing them, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amounts of active ingredient applied depend on the time of the year, the plants to be combated and their growth stage, and vary from 0.01 to 5, and preferably from 0.03 to 0.5, kg/ha.

The herbicidal action of the compounds according to the invention on the growth of test plants is demonstrated in the following greenhouse experiments.

The vessels employed were plastic flowerpots having a volume of 300 m$^3$, which were filled with a sandy loam containing about 3.0% humus. The seeds of the test plants were sown separately, according to species.

For the postemergence treatment, the plants were grown, depending on growth form, to a height of from 3 to 15 cm before being treated with the active ingredients, suspended or emulsified in water as vehicle, by spraying them through finely distributing nozzles. Either plants which had been sown directly in the pots and grown there were selected, or plants which had been grown from seedlings and were transplanted to the vessels. The application rate for postemergence treatment was 0.5 kg/ha.

The pots were set up in the greenhouse—species from warmer areas at from 20° to 36° C., and species from moderate climates at 10° to 20° C. The experiments were run for 2 to 4 weeks. During this period the plants were tended and their reactions to the various treatments assessed.

The scale employed was 0 to 100, 100 denoting nonemergence or complete destruction of at least the visible plant parts, and 0 denoting no damage or normal emergence.

The following plant species were employed for the experiments:

| Abbreviation | Latin name |
|---|---|
| AMARE | Amaranthus retroflexus |
| CASTO | Cassia tora |
| CENCY | Centaurea cyanus |
| ECHGG | Echinochloa crus-galli |
| GALAP | Galium aparine |
| IPOSS | Ipomoea spp. |
| MERAN | Mercurialis annua |
| VIOSS | Viola spp. |

Tables A, B and C show that compounds 1.058, 1.046, 1.032, 1.035 and 1.020 had, on postemergence application, a very strong herbicidal action on a large number of widespread broadleaved plants.

Compound no. 1.076 also proved to be suitable for controlling grassy plants such as *Echinochloa crus-galli* (Table C).

In view of the numerous application methods available, the compounds according to the invention, or herbicidal agents containing them, may be used in a large number of crops for combating unwanted plants. The following may be mentioned by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Triticum durum | durum wheat |

-continued

| Botanical name | Common name |
| --- | --- |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the novel compounds may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, quinolinecarboxylic acids, etc.

It may also be useful to apply the novel compounds, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

TABLE A

Herbicidal action on postemergence application of 0.5 kg/ha in the greenhouse

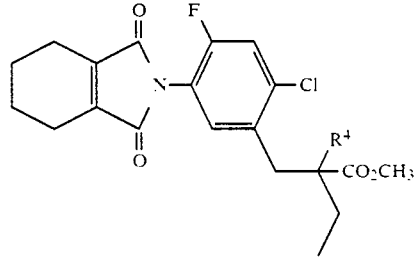

| | | Test plants and damage (%) | | | |
| --- | --- | --- | --- | --- | --- |
| Ex. | R⁴ | AMARE | GALAP | IPOSS | CENCY |
| 1.058 | ethyl | 100 | 98 | 100 | 100 |
| 1.046 | methyl | 100 | 100 | 100 | 100 |

TABLE B

Herbicidal action on postemergence application of 0.5 kg/ha in the greenhouse

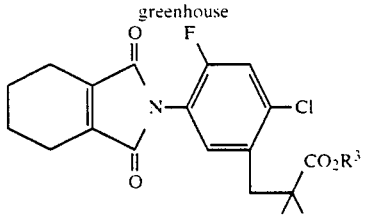

| | | Test plants and damage (%) | | |
| --- | --- | --- | --- | --- |
| Ex. | R³ | GALAP | IPOSS | MERAN |
| 1.032 | CH₂CH₂OCH₃ | 100 | 100 | 100 |
| 1.035 | CH₂CH₂OCH₂CH₃ | 100 | 100 | 100 |

TABLE C

Herbicidal action of comp. no. 1.076 on postemergence application of 0.5 kg/ha in the greenhouse

TABLE C-continued

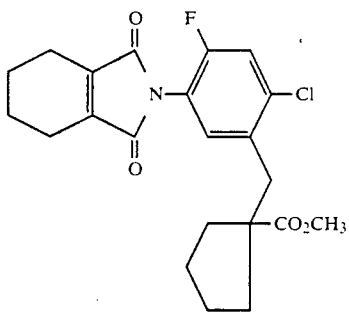

| Test plants | Damage |
|---|---|
| ECHCG | 100 |
| AMARE | 100 |
| GALAP | 100 |
| IPOSS | 100 |
| CENCY | 100 |
| CASTO | 100 |

TABLE D

Herbicidal action of comp. no. 1.020 on postemergence application of 0.5 kg/ha in the greenhouse

| Test plants | Damage |
|---|---|
| IPOSS | 100 |
| CENCY | 100 |
| MERAN | 100 |
| VIOSS | 100 |

We claim:

1. 3-Phenylpropionic acid compounds of the formula I:

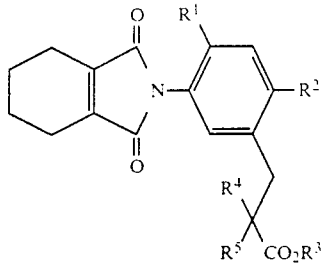

wherein $R^1$ is hydrogen or halogen; $R^2$ is halogen; $R^3$ is $C_2$–$C_6$-alkyl which is substituted by $C_1$–$C_4$-alkoxy or $C_1$–$C_4$-alkylthio; $C_1$–$C_6$-alkyl or $C_1$–$C_6$-alkyl which is substituted by $C_5$–$C_7$-cycloalkyl; $C_5$–$C_7$-cycloalkyl; $C_3$–$C_6$-alkenyl or $C_3$–$C_6$-alkynyl or, $R^3$ together with $R^4$, is $C_2$–$C_4$-alkylene $R^4$ is $C_1$–$C_4$-alkoxy, $C_1$–$C_4$-alkylthio, $C_5$–$C_7$-cycloalkyl-substituted $C_1$–$C_6$-alkyl, –$C_7$-cycloalkyl, $C_3$–$C_6$-alkenyl or halogen-substituted $C_3$–$C_6$-alkenyl or $C_3$–$C_6$-alkynyl, or $R^4$, together with $R^5$, is $C_3$–$C_6$-cycloalkyl which is uninterrupted or interrupted by an oxygen or sulfur atom; and $R^5$ is $C_1$–$C_4$-alkoxy or $C_1$–$C_4$-alkylthio-substituted $C_2$–$C_6$-alkyl; cyano or acyl or the formula $COR^6$ or alkoxycarbonyl of the formula $CO_2R^7$, wherein $R^6$ is $C_1$–$C_6$-alkyl or, together with $R^4$, a $C_3$–$C_5$-alkylene chain and $R^7$ is $C_2$–$C_6$-alkyl which is unsubstituted or substituted by halogen, $C_1$–$C_4$-alkoxy or $C_1$–$C_4$-alkylthio-substituted $C_2$–$C_6$ alkyl or $C_1$–$C_6$-alkyl or $C_5$–$C_7$-cycloalkyl-substituted $C_1$–$C_6$-alkyl or $C_5$–$C_7$-cycloalkyl, $C_3$–$C_6$-alkenyl or $C_3$–$C_6$-alkynyl, with the proviso that $R^1$ and $R^4$ are not simultaneously hydrogen when $R^5$ is cyano or $CO_2R^7$.

2. The 3-phenylpropionic acid compounds of claim 1, wherein $R^1$ is fluorine, and $R^2$ is chlorine or bromine.

3. The 3-phenylpropionic acid compounds of claim 1, wherein said $C_3$–$C_6$-cycloalkyl which is interrupted by oxygen is selected from the group consisting of methyleneoxamethylene, methyleneoxaethylene, methyleneoxapropylene and ethyleneoxaethylene.

4. The 3-phenylpropionic acid compounds of claim 1, wherein said $C_3$–$C_6$-cycloalkyl which is interrupted by sulfur is selected from the group consisting of methylenethiamethylene, methylenethiaethylene, methylenethiapropylene and methylenethiaethylene.

5. The phenylpropionic acid compounds of claim 1, wherein $R^3$ is methyl.

6. A herbicidal composition, comprising an effective amount of a compound of the formula I of claim 1 and a diluent.

* * * * *